US012599875B2

(12) United States Patent
Ritter et al.

(10) Patent No.: US 12,599,875 B2
(45) Date of Patent: Apr. 14, 2026

(54) WINDING SYSTEM FOR WINDING UP CONCATENATED HOLLOW FIBERS ONTO A WINDING CORE

(71) Applicant: enmodes GmbH, Aachen (DE)

(72) Inventors: Ilse Philine Ritter, Aachen (DE); Jens Kaden, Viersen (DE); Ralf Borchardt, Aachen (DE)

(73) Assignee: enmodes GmbH, Aachen (DE)

( * ) Notice: Subject to any disclaimer, the term of this patent is extended or adjusted under 35 U.S.C. 154(b) by 869 days.

(21) Appl. No.: 17/802,285

(22) PCT Filed: Apr. 6, 2021

(86) PCT No.: PCT/EP2021/058939
§ 371 (c)(1),
(2) Date: Aug. 25, 2022

(87) PCT Pub. No.: WO2021/219330
PCT Pub. Date: Nov. 4, 2021

(65) Prior Publication Data
US 2023/0085854 A1     Mar. 23, 2023

(30) Foreign Application Priority Data
Apr. 30, 2020    (DE) ......................... 102020111803.1

(51) Int. Cl.
*B01D 63/02* (2006.01)
*A61M 1/16* (2006.01)

(52) U.S. Cl.
CPC ........... *B01D 63/02* (2013.01); *A61M 1/1698* (2013.01); *B01D 63/0232* (2022.08)

(58) Field of Classification Search
USPC ........................... 242/611, 611.1, 611.2, 612
See application file for complete search history.

(56) References Cited

U.S. PATENT DOCUMENTS

| | | | | | | |
|---|---|---|---|---|---|---|
| 1,558,264 | A | * | 10/1925 | Hathaway | .............. | B65H 75/30 |
| | | | | | | 242/612 |
| 1,962,086 | A | * | 6/1934 | Bixby | .................... | B65H 75/30 |
| | | | | | | 242/612 |

(Continued)

FOREIGN PATENT DOCUMENTS

| | | |
|---|---|---|
| EP | 0089122 A2 | 9/1983 |
| EP | 0216085 A1 | 4/1987 |

(Continued)

*Primary Examiner* — William A. Rivera
(74) *Attorney, Agent, or Firm* — Norris Mclaughlin, P.A.

(57) ABSTRACT

A winding system for winding up concatenated hollow fibers onto a winding core includes a winding core of a device for the mass transfer and/or heat exchange between two media and which winding core is to be inserted together with the hollow fibers wound thereon, into the housing of the device and to remain therein, and at least one coupling element, preferably two coupling elements, wherein the at least one coupling element has two axially opposing connecting regions and is temporarily connectable, by means of the first connecting region, to the winding core for conjoint rotation therewith, and is temporarily connectable, by means of the second connecting region, with a drive for conjoint rotation therewith, the drive being provided for the rotation of the winding core about a winding axis.

14 Claims, 5 Drawing Sheets loaded                    unloaded

(56)                    References Cited

U.S. PATENT DOCUMENTS

| | | | |
|---|---|---|---|
| 2,237,837 A * | 4/1941 | Markle, Jr. ........... | B65H 75/14 |
| | | | 242/118.62 |
| 2,285,732 A * | 6/1942 | Markle, Jr. ........... | B65H 75/14 |
| | | | 242/118.4 |
| 2,731,183 A | 1/1956 | Shaw | |
| 3,255,889 A | 6/1966 | Goldman et al. | |
| 3,783,750 A | 1/1974 | Heimeijer | |
| 3,794,468 A * | 2/1974 | Leonard .............. | B01D 63/026 |
| | | | 96/10 |
| 4,253,228 A | 3/1981 | Easley | |
| 4,289,623 A * | 9/1981 | Lee .................... | A61M 1/1621 |
| | | | 210/247 |
| 4,306,018 A * | 12/1981 | Kirkpatrick ......... | A61M 1/1627 |
| | | | 422/46 |
| 4,666,543 A * | 5/1987 | Kawano ................ | B01D 63/02 |
| | | | 156/169 |
| 4,790,491 A | 12/1988 | Mundus et al. | |
| 4,975,247 A | 12/1990 | Badolato et al. | |
| 5,143,312 A | 9/1992 | Baurmeister | |
| 6,273,355 B1 * | 8/2001 | Van Driel .......... | B01D 63/0233 |
| | | | 242/433.3 |
| 7,172,696 B1 * | 2/2007 | Martinez ............. | B01D 63/025 |
| | | | 96/10 |
| 11,278,652 B2 | 3/2022 | Hiraguchi et al. | |
| 2024/0050635 A1 * | 2/2024 | Zaniboni ................ | B01D 69/08 |

FOREIGN PATENT DOCUMENTS

| | | | |
|---|---|---|---|
| EP | 0285812 A1 | 10/1988 | |
| EP | 3520838 A1 | 8/2019 | |
| FR | 2095979 A5 | 2/1972 | |
| WO | 9733636 A1 | 9/1997 | |

* cited by examiner

WINDING SYSTEM FOR WINDING UP CONCATENATED HOLLOW FIBERS ONTO A WINDING CORE

The invention relates to a winding system for winding up concatenated hollow fibers, in particular mass-permeable and/or energy-permeable hollow fibers, onto a winding core.

From the state of the art, it is known to wind mass-permeable or energy-permeable hollow fibers, in particular such fibers connected with warp threads to form mats, onto a core so that the wound hollow fiber pack can be inserted into a device for the mass transfer and/or energy exchange between two media, in particular an oxygenator and/or a heat exchanger. This is known e.g., from the publications EP 0 089 122 A2 and EP 0 285 812 A1.

For this purpose, the wound hollow fiber pack is inserted into a housing of the transfer device and subsequently, the hollow fiber ends are bonded to one another and to the housing, a process also known as potting. Inside the housing, after opening of the hollow fiber ends, that is, after removing the end-sided bonding, two media can be guided separated by the hollow fiber walls, namely one medium, e.g. blood, outside along the hollow fibers and another medium, e.g. a gas or a gas mixture or a temperate fluid, through the hollow fibers.

Via the hollow fibers, in particular for a mass transfer via semipermeable hollow fibers, an exchange can take place, e.g. in an oxygenator, an exchange of oxygen and carbon dioxide. Such wound hollow fiber packs can also be used in mass transfer devices for dialysis purposes or for the elimination of carbon monoxide.

Winding the hollow fibers onto a core and the integration of the produced package into a transfer device is a complex process which is to be simplified with the invention. In particular, it is another object of the invention to design the winding in such a simplified way that a winding core used for winding can on the one hand be simply adapted to a drive, thus enabling a motorized winding, and on the other hand can also be directly used in the transfer device. In particular, it is an object of the invention to design the adaption of the winding core to the drive in such a way that a fast adaption and a non-residue removal of the adaption is possible.

This object is achieved by a winding system for winding concatenated hollow fibers, in particular mass-permeable and/or energy-permeable hollow fibers, onto a winding core, the system comprising a winding core of an transfer device for the mass transfer and/or heat exchange between two media, in particular of an oxygenator and/or a heat exchanger, onto which winding core concatenated hollow fibers can be wound and which winding core is provided, in particular set up, to be inserted, together with the hollow fibers wound thereon, into the housing of the device and to remain therein, and further comprising at least one coupling element, preferably two coupling elements, wherein the at least one coupling element has two axially opposing connecting regions and is temporarily connectable, by means of the first connecting region, with the winding core for conjoint rotation therewith and is temporarily connectable, by means of the second connecting region, with a drive for conjoint rotation therewith, the drive being provided for the rotation of the winding core about a winding axis, wherein the first connecting region of the coupling element comprises an expansion element, in particular an expansion element the outer cross section of which can be increased by expansion, and the winding core has in at least one axial end face, preferably in both axial end faces, a recess around the winding axis, into which recess the first connecting region of a coupling element can be inserted and in which the winding core can, by means of expansion of the expansion element be connected to the coupling element for conjoint rotation.

The core idea of the winding system is thus that the winding core used with the winding system can, after the hollow fibers and/or hollow fiber mat(s) have been wound thereon, be directly used as carrier of the hollow fibers in the housing of a transfer device, e.g. a mass transfer device, and that for the purpose of the winding, in particular a motorized winding, the winding core can be simply and quickly coupled to a drive.

For this purpose, the winding system according to the invention uses a coupling element or preferably two coupling elements around the winding core opposing one another on a joint axis of rotation by which element or elements the adaption to a drive is established. The attachment of the coupling element at the winding core for conjoint rotation therewith is made by an expansion of the respective coupling element in its first connecting region pointing towards and interacting with the winding core.

Such an expansion may, for example, be made between two expansion positions, wherein in the one expansion position, the connection between the coupling element and the winding core is released, and in the other expansion position, a connection for conjoint rotation is achieved, so that a drive coupled to the second connecting region of the coupling element is able to rotate the winding core and to wind hollow fiber mats guided to the winding core.

Where in the following, the winding core and the coupling element are described in more detail, it should be noted that the description is also correct if at the winding core, a respective coupling element can be attached at both opposing axial end faces. This is a preferred embodiment anyhow. In this case, the description of the winding core applies to both end faces and to either of the two usable coupling elements, in particular, which can be executed so as to be identical.

An expansion connection between the winding core and the coupling element has the advantage that the connection is established without any axial, i.e. translational or rotational movement of the components to be connected in relation to one another when the connection is established. Rather, the expansion connection preferably achieves that as a consequence of the expansion of the expansion element, interacting contact areas move towards one another and contact one another, thereby establishing a frictional connection and/or force connection.

Compared with other kinds of connection, this has the advantage that an abrasion of material between the two components to be connected is avoided, as it could, for example, occur between them if the coupling element were screwed into the winding core. Such potential abraded particles can have negative consequences if the winding core is used in a mass transfer device and these particles are transferred into the mass transfer device and could get into the blood circulation of a patient. In addition, the expansion connection according to the invention has the advantage that it can be produced by injection molding.

The winding core that is used in the winding system and that subsequent to the winding process is inserted into the housing of a transfer device and remains therein for the operation of the device, may e.g. be set up for this use in that the winding core is finally adapted in terms of its geometry or its dimensions to the housing so that it can be inserted into the housing without any modification except the removal of the coupling element or the coupling elements. Further, preferably the winding core can for this purpose also have at least one channel in the interior of the winding core through which channel a medium can be guided during the subsequent operation.

A setting up or suitability of the winding core for this purpose may in a further advantageous embodiment be given in that a recess in the winding core (in particular both recesses) for receiving the coupling element is formed by a channel that at least partly penetrates the winding core, through which channel, after the insertion of the winding core into the housing of the mass transfer device, a medium, in particular blood, can flow. Such a channel hence has two functions, namely both in the winding system for the attachment of the coupling element and in the subsequent mass transfer device for the transport of media.

The channel may, for example, extend through the winding core completely in axial direction, in particular in such a way that two coupling elements can be arranged on both sides of the winding core. In case of two recesses for receiving coupling elements, only one may be formed by a channel that serves for the transport of media, in particular a channel that does not completely extend through the winding core in axial direction.

An above channel may end on one side in the recess for the attachment of the coupling element and at its other end, end in one or several orifices on the lateral area of the winding core, in particular if the channel does not extend axially through the entire winding core.

A through channel may also have branches ending in orifices in the outer lateral area of the winding core.

With orifices in the lateral area of the winding core, it can be achieved that in the subsequent operation, a medium such as blood, can penetrate through these orifices into the wound hollow fiber pack, preferably with a radial inflow component.

Further, a (respective) recess in the winding core for receiving the coupling element may be surrounded by a channel which at least in parts runs coaxial in relation to the recess and through which channel, after insertion of the winding core into the housing of the mass transfer device, a medium, in particular blood, can flow. For such a coaxial channel, the above descriptions may apply in the same way, in particular, it may likewise end in the lateral area of the winding core or have branches ending in the lateral area of the winding core.

Independently of these aforementioned possibilities to obtain a suitability of the winding core for the mass transfer device, the invention may provide at least one coupling element having at its first connecting region a shank which is split axially into at least two axially parallel adjoining shank parts between which a wedge element is provided as an expanding component, which wedge element can be axially moved between the shank parts. When an axial movement of the wedge element between the shank parts is caused, these are thus moved radially outward.

Preferably, the shank has at least three shank parts. The wedge element may preferably be conical or cone section shaped. In its axial movement for the expansion, the wedge element may preferably be movable from the first connecting region in the direction of the second connecting region. To allow a moving force to act on the wedge element, the wedge element may be guided through a hollow section of the shank, e.g. into the second connecting region or out of the second connecting region.

In another embodiment, the at least one coupling element may have at its first connecting region a shank with a shank section around which a sleeve made of an elastic material, in particular an elastomer, preferably a vulcanizate of silicone rubber or natural rubber, is arranged as an expansion element, wherein the sleeve can be changed in its size in radial direction as a result of axial movement of its end faces towards each other, in particular through the application of an axial force on the annular end faces of the sleeve. In particular, the invention may provide that the sleeve in the unconnected state between the coupling element and the winding core is force-free and/or in relaxed condition, and for the connection, an axial force is applied which moves the axial end faces of the sleeve towards each other whereby the sleeve radially bulges.

In a possible embodiment, the sleeve may with a first end of its two axial ends contact a first area of force application of the coupling element, which area is stationary in relation to the shank area, and the sleeve may with the second axial end contact a second area of force application of the coupling element, wherein the second area of force application is movable relative to the first area of force application in axial direction of the sleeve, in particular movable on the shank, preferably by means of an actuating element provided at the coupling element.

The stationary first area of force application may be arranged at the free end of the first connecting region which is inserted into the recess of the winding core. The outer cross section/outside diameter of the area of force application is preferable larger than or the same as the inner cross section/inside diameter of the recess in the winding core.

Irrespective of the kind of the expansion, the invention may preferably provide that in one state of expansion, the position of the coupling element can be axially fixed relative to the winding core, preferably also be axially fixed relative to an auxiliary element separate from the core which auxiliary element can, after the first connecting region of the coupling element has been inserted into the recess of the winding core, be pushed over the coupling element and placed onto an axial end face of the winding core.

The use of an auxiliary element for fixing the coupling element in the recess of the winding core can have several advantages.

Fore example, the auxiliary element may be formed by a disc protruding radially beyond the cross section/diameter of the winding core. Such a disc may preferably be used to position, in particular center, the hollow fiber mat(s) relative to the winding core for the winding, in particular, if at the winding core, coupling elements with respective discs are attached on both sides so that a wound hollow fiber mat positions itself between the discs during the winding.

Further, the auxiliary element for the sleeve may form a second area of force application which can be contacted by the sleeve with the second axial end, in particular the end of the sleeve pointing to the second connecting region of the coupling element, wherein the second end of the sleeve pointing to the second connecting region of the coupling element protrudes beyond the axial end face of the winding core when the coupling element is in its state of insertion in the winding core, and the application of the force on the sleeve can be caused by placing the auxiliary element, in particular as a result of which the second end of the sleeve can be displaced in the direction of the first end of the sleeve.

The invention also provides that the second end of the sleeve pointing to the second connecting area of the coupling element may lie below the axial end face or in the plane of the axial end face of the winding core when the coupling element is in its state of insertion in the winding core, and the application of the force after the placement of the auxiliary element can be caused by an axial movement of the coupling element, in particular a movement directed out from the winding core, in particular as a result of which the first end of the sleeve can be displaced in the direction of the second end of the sleeve.

In both cases, the interaction between the auxiliary element and/or the disc and one of the axial end faces of the sleeve causes a movement of the two end faces of the sleeve towards each other and with this a radial bulging of the sleeve.

Irrespective of the kind of the execution of the expansion element, the invention may provide that the position of the coupling element can be axially fixed, e.g. by means of a retaining ring that can be inserted into an annular groove at the coupling element and that can support the coupling element at the surface of the auxiliary element.

This annular groove may preferably be arranged between the two connecting regions of the coupling element, in particular in a section of the coupling element that transitions into the section which comprises or forms the expansion element, that is, preferably transitions into the shank area which carries the sleeve or which transitions into the wedge element.

In all possible embodiments, an actuating element may be provided at the coupling element, which actuating element can cause an expansion of the first connecting region and/or the axial fixing of the coupling element, in particular an actuating element supported by the auxiliary element or by an element exhibiting the second area of force application or by a supporting element arranged at the coupling element.

An actuating element may be designed e.g. as a nut on a threaded section of the coupling element which is connected with the expansion element. The threaded section may e.g. transition into the shank section which carries the sleeve or into the wedge element.

An actuating element may also be designed as an eccentric that is movable with a lever and can be rotated about an axis and that is supported by the coupling element or the auxiliary element, wherein the section exhibiting the axis transitions into the shank area which carries the sleeve, or transitions into the wedge element. Through the eccentric movement, the axis within the coupling element may be shifted and the expansion element may be actuated, in particular, the sleeve may be compressed or the wedge element may be axially shifted.

The following is a brief description of the drawings.

One embodiment is described by way of example in more detail on the basis of the figures.

Figure 1:
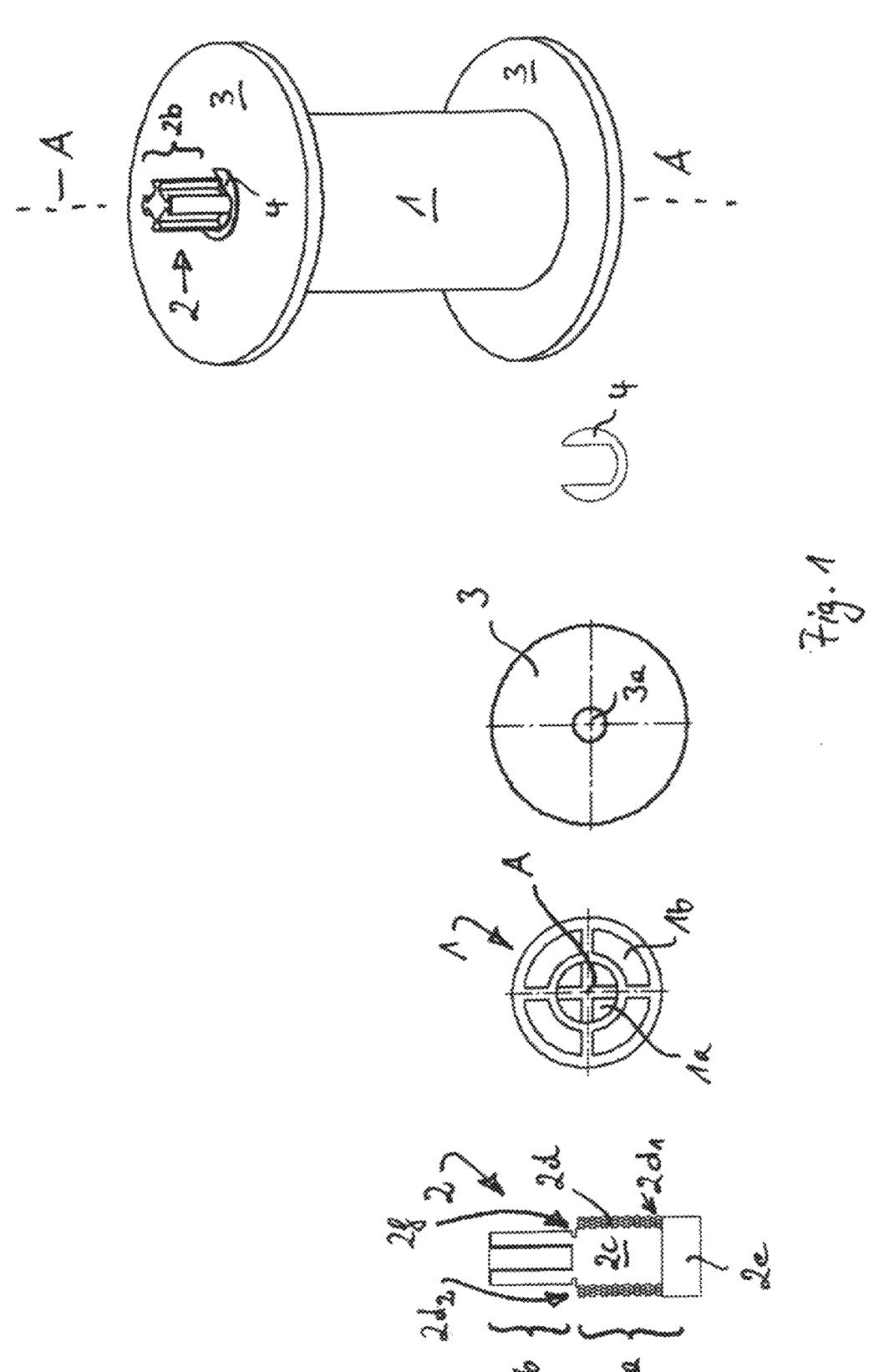
FIG. 1 shows the assembled winding system.

FIG. 1 shows an overview of the components of the winding system.

It comprises a winding core 1 upon which hollow fibers and/or hollow fiber mats, not shown, can be wound. The winding core 1 has a central recess 1a arranged about the winding axis A, preferably in its two opposing end faces, which each preferably extends from the end face into the winding core. The recess is formed by a channel in the winding core. The recess 1a is further coaxially surrounded by a channel 1b, in particular with radial cross members between the walls of both channels 1a, 1b. Such an execution is not absolutely necessary.

Into the recess 1a, shown here with a circular cross section, a coupling element 2 can be inserted. This has a first connecting region 2a fitting into the recess 1a and a second connecting region 2b that is designed for the connection with a drive which is not shown here in more detail. This second connecting region is thus set up to be connected with the drive, e.g. a coupling of the drive, for conjoint rotation.

The coupling element 2 also as a shank area 2c around which a sleeve 2d made of an elastomer, e.g. silicone is arranged as an expansion element. At the free end of the first connecting region 2a, the sleeve with a first axial end 2d1 abuts an area of force application 2e of the coupling element. The second axial end 2d2 of the sleeve 2d is free. By axial compression of the sleeve 2d, that is by applying a force which moves the axial ends 2d1 and 2d2 towards each other, the sleeve 2d can be caused to radially bulge.

The winding system may further comprise an auxiliary element 3 which may be designed as disc 3. This disc has an inner opening 3a with can be pushed over the second connecting region 2b of the coupling element 2. The outside diameter of the disc 3 is larger than the outside diameter of the winding core 1.

In a possible development, the winding system also comprises a retaining ring 4 that can be inserted into an annular groove 2f between the connecting regions 2a and 2b of the coupling element 2.

The right part of FIG. 1 shows the assembled winding system, after the coupling element 2 has been inserted into the recess 1a of the winding core 1 and the disc 3 has been pushed over the coupling element 2 and has been placed on the end face of the winding core 1.

Figure 2:
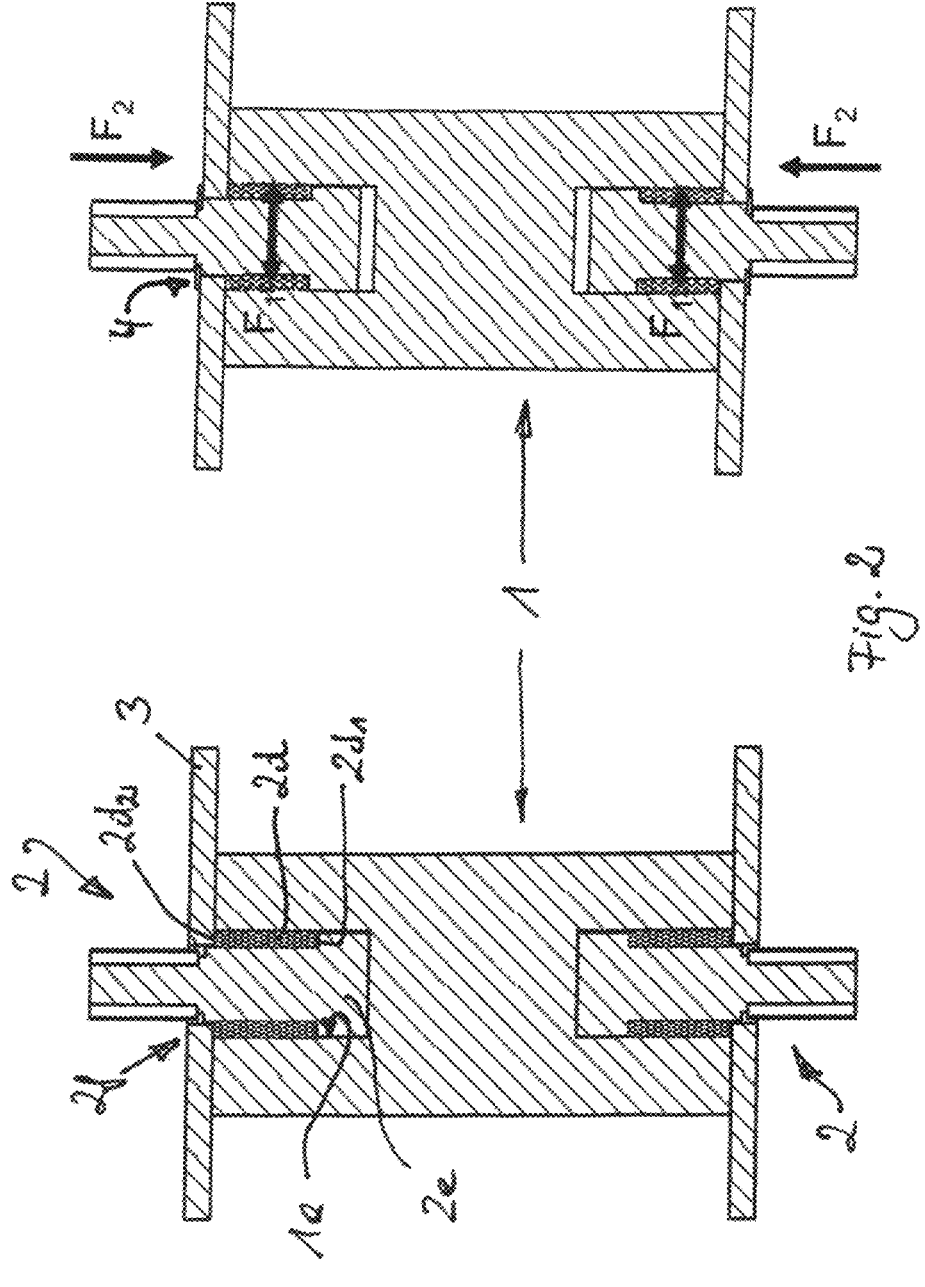
FIG. 2 shows a section of the assembled winding system in two states.

FIG. 2 shows a section of the assembled winding system in two states.

In the left part of FIG. 2, it can be seen that the coupling element 2 has been inserted into the recess 1a of the winding core 1 without the expansion element 2d, in this case, the sleeve 2d, being expanded, i.e. bulged. The disc 3 lies on the end face of the winding core 1 and can preferably have contact with the second axial end face 2d2 of the sleeve 2d already in the unloaded state. For this purpose, the second axial end 2d2 of the sleeve lies in the plane of the end face of the winding core. The second axial end 2d2 of the sleeve may alternatively also lie below the plane of the end face of the winding core and in the initial state not have contact with the auxiliary element.

The annular groove 2f of the coupling element 2 lies below the surface of the disc 3 and is not accessible to the retaining ring 4.

The connecting region 2a lies fully within the winding core 1 without being connected with same. The connecting region 2b lies outside the winding core 1 and is accessible for coupling to a drive that is not shown.

For attaching the coupling element 2 in the winding core 1, the sleeve is expanded which is achieved by the coupling element being pulled for a certain distance out of the recess, at least until the annular groove becomes accessible above the disc 3. This way, the area of force application 2e is moved in the direction of the disc 3. Since the sleeve 2d is contained between the area of force application 2e and the disc 3, the movement of the area of force application 2e axially compresses the sleeve 2d which thus bulges. As a consequence, the lateral area of the sleeve 2d is pressed against the inner surface of the recess 1a which causes a frictional connection with the radially acting force F1 as shown in the right part of FIG. 2.

The right part of FIG. 2 shows the retaining ring 4 inserted into the annular groove 2f so that the coupling element 2 cannot return again into the recess 1a. As a result, the force F1 continues to act statically and the coupling element is caught in the recess 1a of the winding core 1.

Further, a force F2 is applied with is caused by the sleeve 2d pulling back the coupling element 2 into the recess 1a due to its axial compression, but such pulling back is not possible because of the support of the retaining ring 4 on the disc 3. The force F2 thus acts via the retaining ring 4 on the disc 3 and presses this additionally against the end face of the winding core 1.

In expanded state shown in the right part of FIG. 2, the winding core 1 can be connected on both sides to a drive to wind the at least one hollow fiber mat onto the winding core.

After this winding is complete, the winding core can be separated from the drive, the retaining ring 4 can be pulled off the respective coupling element 2 and both can be removed from the winding core 1 together with the disc 3.

The winding core can then together with the hollow fibers it carries be inserted into the housing of a transfer device and the hollow fibers can thus be potted/encapsulated. The channel 1a and/or 1b in the winding core can preferably be used for the transport of medium, e.g. blood, through the winding core.

Figure 3:
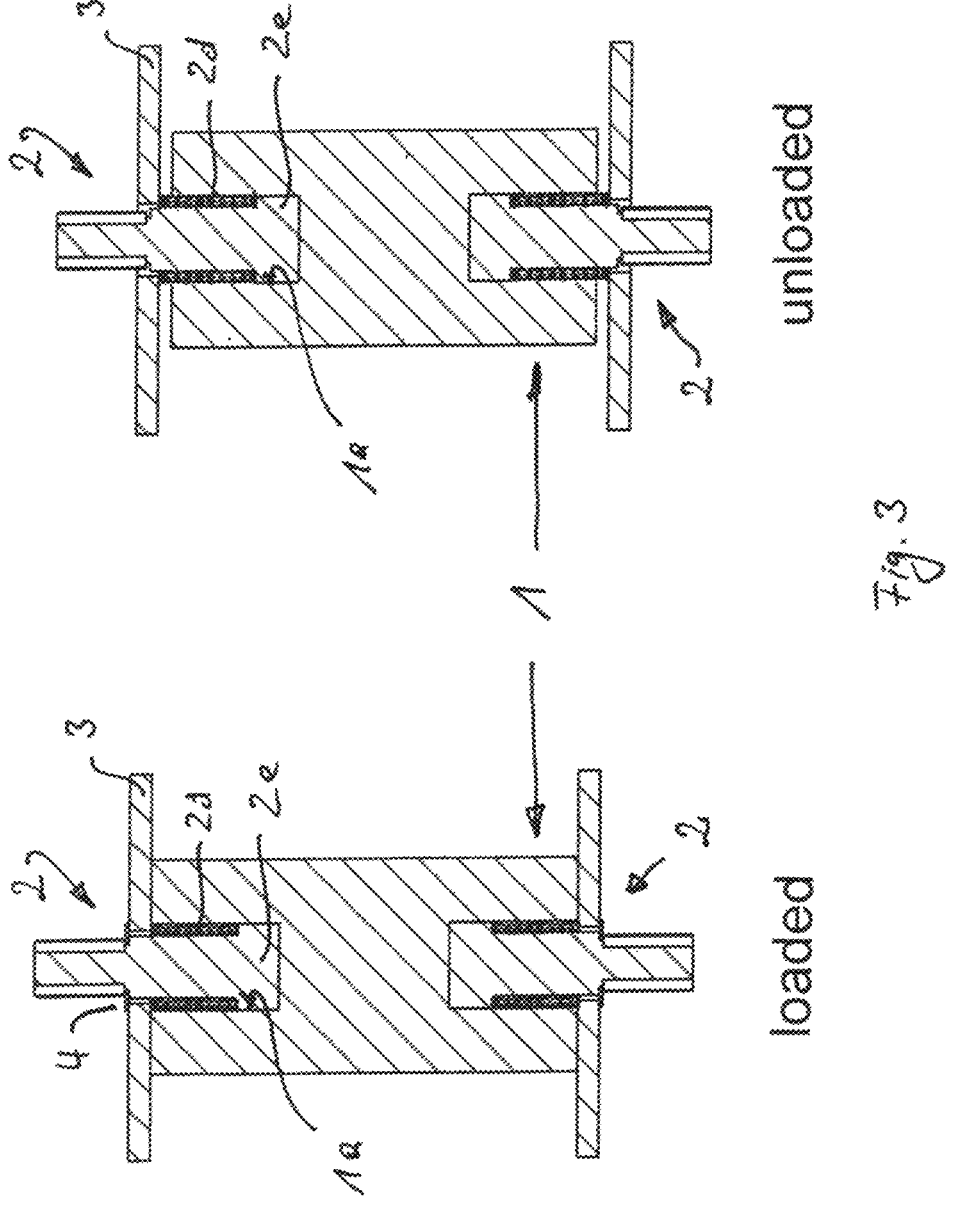
FIG. 3 shows in its right part and left part respective two embodiments.

FIG. 3 shows in its right part an embodiment where in the not-expanded state after the insertion of the coupling element 2 into the winding core 1, the sleeve 2d protrudes with its axial end 2d2 beyond the end face of the winding core 1 and thus is axially compressed when the disc 3 is placed as an auxiliary element, whereby the sleeve bulges and the frictional connection is established. The left part of FIG. 3 shows the axial securing of the situation created this way with the retaining ring 4, as in the right part of FIG. 2. In other respects, FIG. 3 corresponds to the embodiment of FIG. 2.

Figure 4:
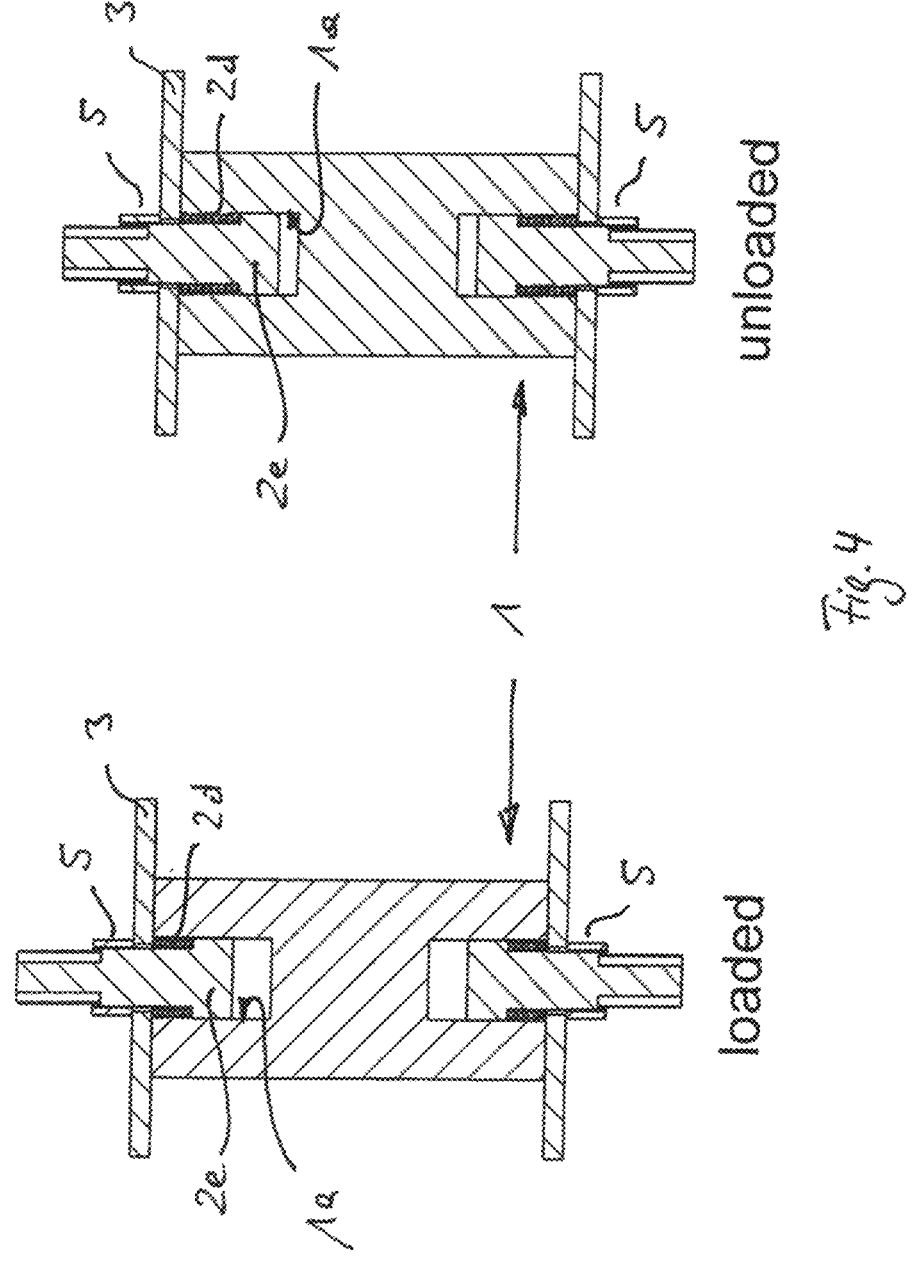
FIG. 4 shows an alternative embodiment.

FIG. 4 shows an alternative embodiment to realize the attachment of the coupling element 2.

The coupling element 2 has between the connecting region 2b for the connection with a drive and the axial end 2d2 of the sleeve 2d a section with an external thread onto which a ring 5 or a nut 5 with a corresponding internal thread can be screwed, e.g. after the disc 3 has been pushed over the connecting region 2b and placed on the end face of the winding core 1. After the ring 5 being screwed on has made contact with the disc 3, the ring 5 pulls the coupling element 2 in axial direction out of the winding core for a certain distance, whereby the sleeve 2d which has with its upper axial end 2d2 contact with the disc 3 is axially compressed and thus radially expands/bulges. This establishes the frictional connection. The right part of FIG. 4 shows the not expanded state and the left part of FIG. 4 shows the expanded state.

Figure 5:
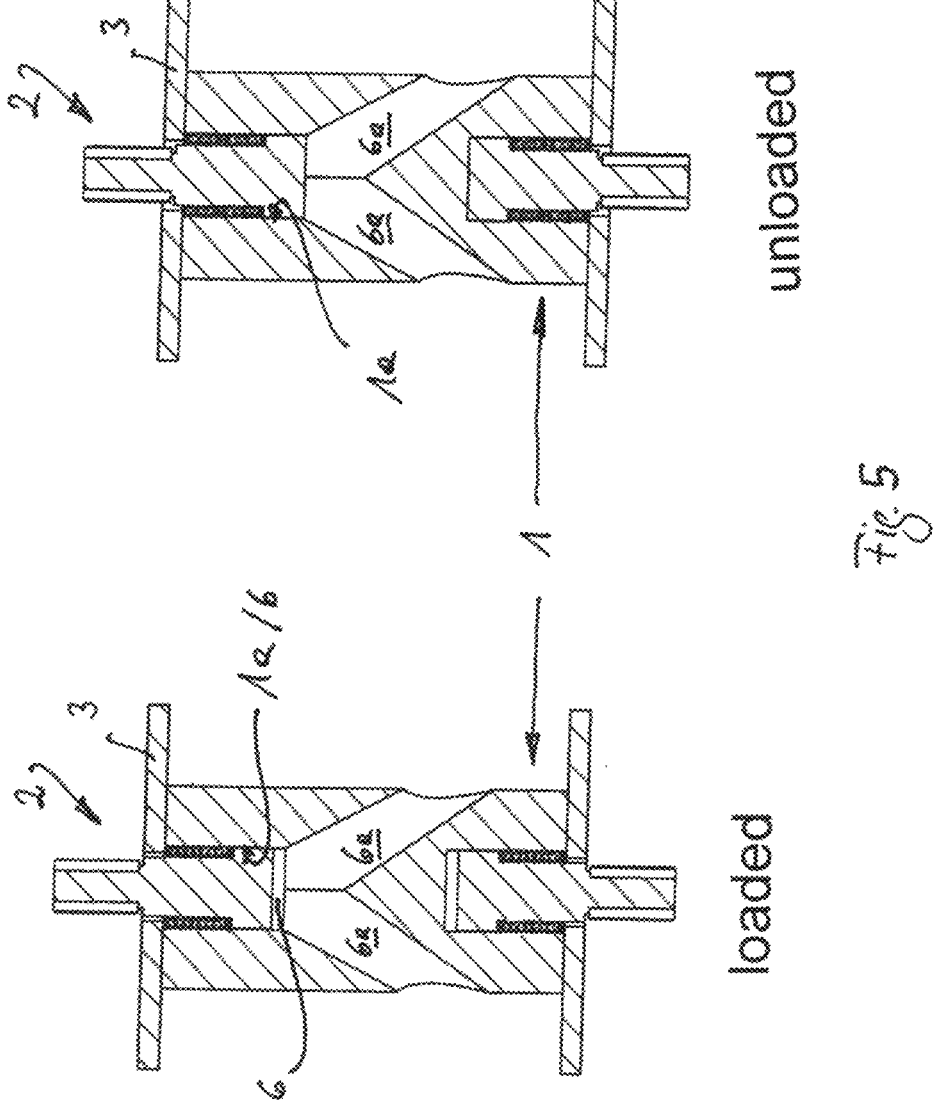
FIG. 5 shows an embodiment which is independent of the kinds of expansion.

FIG. 5 shows a possible embodiment that may be selected independent of the kinds of the possible expansion. By way of example, the shown expansion is the same as in FIG. 2. Referring to FIG. 5, the upper recess 1a in the winding core 1 is designed as a channel 6 which starts at the upper end face of the winding core 1 and extends into the same and branches into channel sections 6a which end in the lateral area of the winding core 1. This way, a medium guided through this channel can flow to hollow fibers from radially inside. The left part of FIG. 5 shows the coupling element 2 in expanded state and the right part shows it in not expanded state.

What is claimed:

1. A winding system for winding concatenated hollow fibers onto a winding core, the system comprising:

a. a winding core of a transfer device for the mass transfer and/or heat exchange between two media, the winding core being configured to have concatenated hollow fibers wound thereon and the winding core being configured to be inserted, together with the hollow fibers wound thereon, into a housing of the device and to remain therein, and b. at least one coupling element, wherein each of the at least one coupling element has first and second axially opposing connecting regions and is configured to be temporarily connectable, by means of the first connecting region, with the winding core for conjoint rotation therewith and is configured to be temporarily connectable by means of the second connecting region, with a drive for conjoint rotation therewith, the drive being configured to rotate the winding core about a winding axis, wherein the first connecting region of the coupling element comprises an expansion element configured so that the outer cross section thereof can be increased by expansion, and the winding core has in at least one axial end face a recess around the winding axis configured for insertion therein of the first connecting region of the coupling element of one of the at least one coupling element thereby to connect the winding core to the coupling element by means of expansion of the expansion element for conjoint rotation therewith, and the first connecting region of each of the at least one coupling element comprises a shank having a shank section around which a sleeve made of an elastic material is arranged as the expansion element, wherein the sleeve is configured to be changed in its size in radial direction as a result of axial movement of annular end faces of the sleeve towards each other through application of an axial force on the annular end faces of the sleeve.

2. The winding system according to claim 1, wherein each of the at least one coupling element is configured so that a first of the annular end faces thereof contacts a first area of force application of the coupling element, which area is stationary in relation to the shank area, and a second of the annular end faces thereof contacts a second area of force application of the coupling element, the second area of force application being configured to be movable on the shank relative to the first area of force application in axial direction of the sleeve.

3. The winding system according to claim 2, wherein each of the at least one coupling element is configured so that in one state of expansion thereof, a position of the coupling element can be axially fixed relative to the winding core and relative to an auxiliary element separate from the winding core which auxiliary element (3) can, after the first connecting region of the coupling element has been inserted into the recess of the winding core, be pushed over the coupling element and placed onto one of the axial end faces of the winding core.

4. The winding system according to claim 3, wherein the auxiliary element comprises a disc protruding radially beyond a radial cross section of the winding core and configured to position a mat of the concatenated hollow fibers relative to the winding core during the winding.

5. The winding system according to claim 3, wherein the auxiliary element is configured to form the second area of force application which can be contacted by the second annular end face of the sleeve pointing to the second connecting region of the coupling element, wherein

9 a. the second annular end face of the sleeve pointing to the second connecting region of the coupling element protrudes beyond the axial end face of the winding core when the coupling element is in its state of insertion in the winding core, and the auxiliary element is configured so that the application of force on the sleeve can be caused by the auxiliary element displacing the second annular end face of the sleeve in a direction of the first annular end face of the sleeve, or b. the second annular end face of the sleeve pointing to the second connecting area of the coupling element lies below the axial end face or in the plane of the axial end face of the winding core when the coupling element is in its state of insertion in the winding core and the coupling element is configured so that application of force and resulting expansion of the coupling element can be caused by an axial movement of the coupling element directed out from the winding core as a result of which the first annular end face of the sleeve can be displaced in a direction of the second annular end of the sleeve.

6. The winding system according to claim 5, further comprising a retaining ring configured to be inserted into an annular groove at the coupling element and support the coupling element at a surface of the auxiliary element and axially fix the coupling element relative to the winding core.

7. The winding system according to claim 6, wherein at the coupling element an actuating element is provided which is configured to cause an expansion of the expansion element in the first connecting region and/or an axial fixing of the coupling element, the actuating element being supported by the auxiliary element or by an element providing the second area of force application or by a supporting element arranged at the coupling element, wherein the actuating element comprises a nut on a threaded section of the coupling element which is connected with the expansion element or the actuating element comprises an eccentric configured to be rotatable about an axis be means of a lever.

8. The winding system according to claim 2, wherein the second area of force application is configured to be movable on the shank relative to the first area of force application in axial direction of the sleeve by means of an actuating element provided at the coupling element.

9. The winding system according to claim 1, wherein the recess in the winding core is formed by a channel that at least partly penetrates the winding core, the channel being configured for flow of blood therethrough after the insertion of the winding core into a housing of the transfer device, wherein the transfer device is a mass transfer device.

10. The winding system according to claim 1, wherein the recess in the winding core is surrounded by a channel which at least in part runs coaxial in relation to the recess, the channel being configured for flow of blood therethrough after insertion of the winding core into a housing of the transfer device, wherein the transfer device is a mass transfer device.

11. The winding system according to claim 1, wherein the transfer device comprises an oxygenator or a heat exchanger.

12. The winding system according to claim 1, wherein the at least one coupling element comprises two coupling elements.

13. The winding system according to claim 12, wherein a respective said recess is provided in each of the axial end faces of the winding core.

14. A winding system for winding concatenated hollow fibers onto a winding core, the system comprising:

a. a winding core of a transfer device for the mass transfer and/or heat exchange between two media, the winding core being configured to have concatenated hollow fibers wound thereon and the winding core being configured to be inserted, together with the hollow fibers wound thereon, into a housing of the device and to remain therein, and b. at least one coupling element, wherein each of the at least one coupling element has first and second axially opposing connecting regions and is configured to be temporarily connectable, by means of the first connecting region, with the winding core for conjoint rotation therewith and is configured to be temporarily connectable by means of the second connecting region, with a drive for conjoint rotation therewith, the drive being configured to rotate the winding core about a winding axis, wherein the first connecting region of the coupling element comprises an expansion element configured so that the outer cross section thereof can be increased by expansion, and the winding core has in at least one axial end face a recess around the winding axis configured for insertion therein of the first connecting region of the coupling element of one of the at least one coupling element thereby to connect the winding core to the coupling element by means of expansion of the expansion element for conjoint rotation therewith, and the first connecting region of each of the at least one coupling element comprises a shank which is split axially into at least two axially parallel adjoining shank parts between which a wedge element is provided as an expanding component, the wedge element being configured to be moved axially between the shank parts.

* * * * *